US009284548B2

(12) United States Patent
Collinson et al.

(10) Patent No.: US 9,284,548 B2
(45) Date of Patent: Mar. 15, 2016

(54) HIGH AFFINITY ADAPTOR MOLECULES FOR REDIRECTING ANTIBODY SPECIFITY

(75) Inventors: Albert Collinson, Marlborough, MA (US); Peter Wagner, Braunschweig (DE); Matti Sällberg, Stockholm (SE); Anders Vahlne, Stockholm (SE); Gregor Schürmann, Hannover (DE); Robert Kamen, Sudbury, MA (US)

(73) Assignee: Tripep AB, Huddinge (SE)

(*) Notice: Subject to any disclaimer, the term of this patent is extended or adjusted under 35 U.S.C. 154(b) by 46 days.

(21) Appl. No.: 13/497,332

(22) PCT Filed: Oct. 5, 2010

(86) PCT No.: PCT/US2010/051484
§ 371 (c)(1),
(2), (4) Date: Jul. 10, 2012

(87) PCT Pub. No.: WO2011/044133
PCT Pub. Date: Apr. 14, 2011

(65) Prior Publication Data

US 2012/0271033 A1 Oct. 25, 2012

Related U.S. Application Data

(60) Provisional application No. 61/248,778, filed on Oct. 5, 2009, provisional application No. 61/257,351, filed on Nov. 2, 2009.

(51) Int. Cl.

| | |
|---|---|
| ***C40B 30/04*** | (2006.01) |
| ***C12N 15/10*** | (2006.01) |
| ***C40B 40/08*** | (2006.01) |
| ***C40B 50/06*** | (2006.01) |

(52) U.S. Cl.
CPC ........... *C12N 15/1062* (2013.01); *C40B 40/08* (2013.01); *C40B 50/06* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 7,534,435 | B2 | 5/2009 | Sallberg et al. |
| 2003/0129587 | A1 | 7/2003 | Sallberg |
| 2003/0225251 | A1 | 12/2003 | Sallberg et al. |

FOREIGN PATENT DOCUMENTS

| | | | |
|---|---|---|---|
| WO | WO 95-08577 A1 | | 3/1995 |
| WO | WO98/31700 A1 | | 7/1998 |
| WO | 0224887 A2 | | 3/2002 |
| WO | WO03/018773 A2 | | 3/2003 |
| WO | 2005012359 A2 | | 2/2005 |

OTHER PUBLICATIONS

Kolonin et al. (Mar. 31, 2006) The FASEB Journal vol. 20 pp. 979 to 981 and E99 to E107.*

(Continued)

*Primary Examiner* — Christian Boesen
(74) *Attorney, Agent, or Firm* — Lathrop & Gage LLP; James H. Velema, Esq.

(57) ABSTRACT

Disclosed are methods for identifying high affinity adaptor molecules that bind to both a circulating antibody and a target molecule and redirect the specificity of the circulating antibody to the target molecule. Exemplary high affinity adaptor molecules are also provided.

20 Claims, 8 Drawing Sheets

(56) References Cited

OTHER PUBLICATIONS

Hamadeh et al. (Apr. 1992) The Journal of Clinical Investigation vol. 89 pp. 1223 to 1235.*
Castronovo et al. (1989) Journal of the National Cancer Institute vol. 83 pp. 212 to 216.*
Verheije, M. et al,. "Redirecting Coronavirus to a Nonnative Receptor through a Virus-Encoded Targeting Adapter", Journal of Virology, Feb. 2006, vo1.80, No. 3, pp. 1250-1260.
International Search Report & Written Opinion from PCT/US2010/051484, dated Jun. 21, 2011.
Extended European Search Report, EP10822534.3, dated Mar. 21, 2013.
Galili et al. (1999) "Significance of α-Gal (Galα1-3Galβ1-4GlcNAc-R) Epitopes and αl, 3 Galactosyltransferase in Xenotransplantation," Trends in Glycoscience and Glycotechnology. 11(62):317-327.

* cited by examiner

| | |
|---|---|
| CS4541<br>07-090 | H-Gly-D-Val-D-Gln-D-Glu-D-Asp-D-Val-D-Ser-D-Ser-D-Thr-D-Leu-Gly-D-Ser-D-Trp-D-Val-D-Leu-D-Leu-D-Pro-D-Phe-D-His-D-Arg-Gly-D-Thr-D-Arg-D-Leu-D-Ser-D-Val-D-Trp-D-Val-D-Thr-PEG2-Cys-NH2 |
| CS4542<br>07-091 | H-Gly-Gly-D-Phe-D-Glu-Gly-D-Leu-D-Ser-D-Gln-D-Ala-D-Arg-D-Lys-D-Asp-D-Gln-D-Leu-D-Trp-D-Leu-D-Phe-D-Leu-D-Met-D-Gln-D-His-D-Ile-D-Arg-D-Ser-D-Tyr-D-Arg-D-Thr-D-Ile-D-Thr-PEG2-Cys-NH2 |
| CS4543<br>07-092 | H-Gly-D-Val-Gly-Gly-D-Ser-D-Arg-D-Leu-D-Glu-D-Ala-D-Tyr-D-Lys-D-Lys-D-Asp-D-His-D-Arg-D-Val-D-Phe-D-Gln-D-Met-D-Ala-D-Trp-D-Leu-D-Gln-D-Tyr-D-Tyr-D-Trp-D-Ser-D-Thr-D-Thr-PEG2-Cys-NH2 |
| CS3726<br>07-81-1 | H-Gly-D-Ser-Gly-D-Ser-Gly-D-Asn-D-Ala-D-Leu-D-His-D-Trp-D-Val-D-Cys-D-Ala-D-Ser-D-Asn-D-Ile-D-Cys-D-Trp-D-Arg-D-Thr-D-Pro-D-Trp-D-Ala-Gly-D-Gln-D-Leu-D-Trp-Gly-D-Leu-D-Val-D-Arg-D-Leu-D-Thr-PEG2-NH2 |

*Fig. 4*

SEQUENCE LISTING

```
<160> NUMBER OF SEQ ID NOS: 7

<210> SEQ ID NO 1
<211> LENGTH: 29
<212> TYPE: PRT
<213> ORGANISM: Artificial Sequence
<220> FEATURE:
<223> OTHER INFORMATION: Synthetic VEGF-binding peptide

<400> SEQUENCE: 1

Gly Val Gln Glu Asp Val Ser Ser Thr Leu Gly Ser Trp Val Leu Leu
1               5                   10                  15

Pro Phe His Arg Gly Thr Arg Leu Ser Val Trp Val Thr
            20                  25


<210> SEQ ID NO 2
<211> LENGTH: 29
<212> TYPE: PRT
<213> ORGANISM: Artificial Sequence
<220> FEATURE:
<223> OTHER INFORMATION: Synthetic VEGF-binding peptide

<400> SEQUENCE: 2

Gly Gly Phe Glu Gly Leu Ser Gln Ala Arg Lys Asp Gln Leu Trp Leu
1               5                   10                  15

Phe Leu Met Gln His Ile Arg Ser Tyr Arg Thr Ile Thr
            20                  25


<210> SEQ ID NO 3
<211> LENGTH: 29
<212> TYPE: PRT
<213> ORGANISM: Artificial Sequence
<220> FEATURE:
<223> OTHER INFORMATION: Synthetic VEGF-binding peptide

<400> SEQUENCE: 3

Gly Val Gly Gly Ser Arg Leu Glu Ala Tyr Lys Lys Asp His Arg Val
1               5                   10                  15

Phe Gln Met Ala Trp Leu Gln Tyr Tyr Trp Ser Thr Thr
            20                  25


<210> SEQ ID NO 4
<211> LENGTH: 33
<212> TYPE: PRT
<213> ORGANISM: Artificial Sequence
<220> FEATURE:
<223> OTHER INFORMATION: Synthetic VEGF-binding peptide

<400> SEQUENCE: 4

Gly Ser Gly Ser Gly Asn Ala Leu His Trp Val Cys Ala Ser Asn Ile
1               5                   10                  15
```

-continued

```
Cys Trp Arg Thr Pro Trp Ala Gly Gln Leu Trp Gly Leu Val Arg Leu
            20                  25                  30

Thr


<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

Tyr Trp Arg Tyr
1


<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Thr Trp Arg Tyr
1


<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Arg Trp Arg Tyr
1
```

HIGH AFFINITY ADAPTOR MOLECULES FOR REDIRECTING ANTIBODY SPECIFITY

RELATED APPLICATIONS

The present application claims the benefit of priority of International Application No. PCT/US2010/051484 filed Oct. 5, 2010, which claims priority to U.S. Provisional Application No. 61/248,778 filed Oct. 5, 2009 and U.S. Provisional Application No. 61/257,351 filed Nov. 2, 2009, The entire contents of each of the above documents are incorporated herein by reference.

BACKGROUND OF THE INVENTION

The concept of redirecting the immune system to attack new targets has long interested scientists as an appealing strategy for targeted immunotherapy. By redirecting naturally circulating human antibodies to attack desired targets in disease areas such as cancer, autoimmune disease and infectious disease, one can avoid the need for a special immunization. While this strategy has shown early signs of success, most studies have not progressed beyond in vitro demonstrations. For example, this strategy would be particularly valuable if it made use of antibody already present in the general population and could be made amenable to oral administration. Thus, there is a need in the art for improved methods of redirecting antibody specificity.

SUMMARY OF THE INVENTION

The present invention provides isolated adaptor molecules, particularly bispecific adaptor peptides, which bind to both an antibody and a desired target molecule with high binding affinity and selectivity. Due to their high binding affinity and selectivity, the adaptor molecules of the invention are capable of efficiently redirecting circulating antibodies to a target molecule not normally bound by the antibody molecule. Moreover, the adaptor molecules disclosed herein provide one or more of the following advantages over traditional antibody-mediated therapeutics: 1) enable the simultaneous recruitment of multiple antibody-class effector functions; 2) can be developed rapidly using the methods of the invention; 3) have a low cost of goods; and 4) do not cause an IgE-mediated hypersensitivity reaction when administered to a subject.

The adaptor molecules generally comprise one or more targeting moietics linked to one or more ligand moietics. In certain embodiments, the ligand moiety comprises one or more Gal antigen (e.g., Gal-α-1-3-Gal) or mimetic thereof. In one embodiment, the targeting moiety comprises a peptide, e.g., a VEGF or TNFα-binding peptide. Exemplary VEGF-binding peptides have one or more of the amino acid sequences set forth in SEQ ID NO. 1, 2, 3, and/or 4, In another preferred embodiment, the peptide (e.g., the peptide sequence set forth in SEQ ID NO. 1, 2, 3, and/or 4) is linked to a ligand moiety comprising one or more Gal antigens (e.g., Gal-α-1-3-Gal disachharide).

In other embodiments, the targeting moiety comprises one or more antibody, or antigen binding fragment thereof. Suitable antibodies include, without limitation, Abciximab, Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Omalizumab, Palivizumab, Panitumumab, Ranibizumab, Rituximab, Tositumomab, Trastuzumab, and/or Golimumab, or antigen binding fragments thereof. In a preferred embodiment, the antibody (e.g., one or more of the antibodies disclosed supra) or antigen binding fragments thereof, is linked to a ligand moiety comprising one or more Gal antigens (e.g., Gal-α-1-3-Gal). In another preferred embodiment, the antibody (e.g., one or more of the antibodies disclosed supra) or antigen binding fragments thereof, is linked to a ligand moiety comprising one Gal-α-1-3-Gal disaccharide. In another preferred embodiment, a ligand moiety comprising one or more Gal antigens (e.g., Gal-α-1-3-Gal) is linked to one or more variable regions of the antibody.

In other embodiments, the targeting moiety comprises an antibody-like molecule. Suitable antibody-like molecules include, without limitation, Adnectins, Affibodies, DARPins, Anticalins, Avimers, and Versabodies, or antigen binding fragment thereof. In a preferred embodiment, the antibody-like molecule is linked to a ligand moiety comprising one or more Gal antigens (e.g., Gal-α-1-3-Gal).

In other embodiments, the targeting moiety of the invention comprises an extracellular portion of a cell surface receptor, or fragment thereof. Suitable cell surface receptors include, without limitation, a TNF family receptor (e.g., a TNFα receptor, e.g., a human TNFα receptor) and growth factor receptors of the tyrosine kinase family, (e.g, p185HER2). In a preferred embodiment, the extracellular portion of a cell surface receptor molecule is linked to a ligand moiety comprising one or more Gal antigens (e.g., Gal-α-1-3-Gal). In another preferred embodiment, the extracellular portion of a cell surface receptor molecule is linked to a ligand moiety comprising one Gal-α-1-3-Gal disaccharide.

In other embodiments, the targeting moiety comprises a ligand for a cell surface receptor. In a preferred embodiment, the ligand is linked to a ligand moiety comprising one or more Gal antigens (e.g., Gal-α-1-3-Gal). In another preferred embodiment, the ligand is linked to a ligand moiety comprising one Gal-α-1-3-Gal disaccharide.

In another aspect, the invention also provides methods for identifying isolated adaptor molecules, such methods comprising: providing a randomized library encoding a population of candidate targeting moietics; selecting a targeting moiety from the display library which binds with high affinity and/or selectivity to a target molecule; linking the targeting moiety to a ligand moiety via a linking moiety to form a candidate adaptor molecule; and evaluating the ability of the candidate adaptor molecule to redirect the specificity of the circulating antibody to the target molecule. Suitable screening methods for use in the methods of the invention include an mRNA display, ribosome display, yeast display, phage display or screening of synthetic peptide library. In one preferred embodiment, an mRNA display library is used to select a targeting peptide. In another preferred embodiment, a phage display library is used to select a targeting peptide.

A further aspect of the invention provides a method of treating a disease (e.g., a cancer, an infectious disease, or an autoimmune disease) in a subject, comprising administering to the subject an effective amount of an isolated adaptor molecule of the invention, thereby treating the disease. In specific embodiments the disease is at least one of macular degeneration, diabetic retinopathy, psoriasis, diabetes, cardiovascular ischemia, rheumatoid arthritis, and osteoarthritis.

BRIEF DESCRIPTION OF THE FIGURES

FIG. 4 depicts four exemplary high affinity VEGF targeting peptides of the invention.

DETAILED DESCRIPTION

Figure 1:
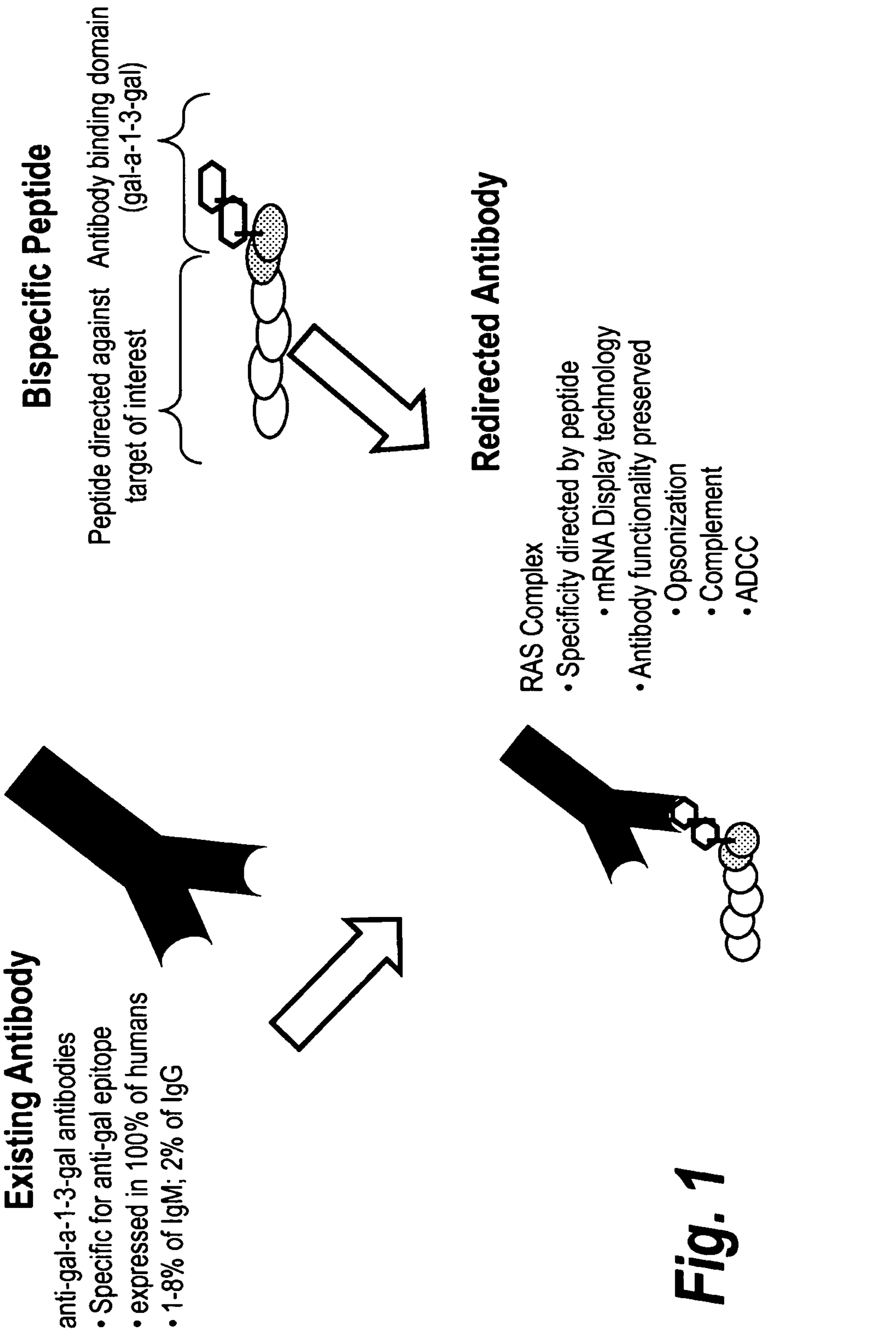
FIG. 1 is a schematic overview of an exemplary adaptor molecule of the invention. The adaptor molecule is a bispecific peptide comprising a high-affinity peptide targeting moiety directed against a target of interest and a ligand moiety comprising the glycopeptide epitope of an anti-gal antibody. By binding to both the target molecule and a naturally-existing anti-gal antibody, the adaptor molecule is capable of redirecting the effector functions of the antibody to act on the target molecule.

This specification describes, inter alia, the identification and production of novel, adaptor molecules that bind to both antibodies and target molecules with high binding affinity and selectivity. As used herein, the term "adaptor" refers to the ability of the peptide to facilitate a functional interaction between an antibody and a target molecule to which the antibody does not normally bind. For example, the adaptor molecules of the invention are capable of binding to both an antibody and a target molecule such that the antibody and target are brought into close proximity with each other. In certain embodiments, the antibody is capable of facilitating an antibody response against the target molecule. Exemplary antibody responses may include neutralization or opsonization of a target molecule (e.g., a soluble factor such as a cytokine or growth factor). Alternatively, where the target molecule is present on the surface of virus, the antibody may facilitate neutralization or opsonization of the virus. In other embodiments, the target molecule may present on the surface of a cell (e.g., an infected cell or tumor cell) and recruitment of the antibody to the cell by the adaptor peptide facilitates the induction of an antibody-mediated effector response (e.g., induction of a complement carcase or antibody-dependent cellular cytotoxicity (ADCC)). The adaptor molecules disclosed herein are particularly advantageous in that they do not appreciably activate basophils, and therefore do not cause an IgE hypersensitivity reaction when administered to a subject.

Adaptor molecules of the invention comprise at least three moieties: (a) a targeting moiety, (b) a ligand moiety and (c) a linker moiety. The targeting moiety (a) is a moiety which binds with high affinity and/or selectivity to a target molecule. The ligand moiety (b) is a moiety to which a circulating antibody binds with high affinity and/or selectivity. The targeting moiety and ligand moiety are operably linked via the intervening linker moiety (c). Said linker moiety may be a covalent bond, chemical linker, or peptide amino acid sequence, or any other moiety capable of linking the targeting and ligand moieties of the adaptor peptide.

(a) Targeting Moiety

A targeting moiety of the invention has been selected for its ability to bind with high affinity and/or selectivity to a target molecule. In particular embodiments, the targeting moiety specifically binds to the target molecule with a dissociation constant (ICD) of 100 nanomolar or less (e.g., 10 nM or less, 1 nM or less, 100 pM or less, 10 pM or less, or 1 pM or less). In other embodiments, the targeting moiety exhibits high selectivity. By "specifically binds" is meant that the moiety recognizes and interacts with a target molecule but that does not substantially recognize and interact with other molecules in a sample, e.g., a biological sample. In particular embodiments, the binding affinity of the targeting moiety for the target molecule is at least 1000 fold higher than its binding affinity for a non-target molecule (e.g., $10^3$ fold, $10^4$ fold, $10^5$ fold, $10^6$ fold, or $10^7$ fold higher).

Targeting moieties can be selected for the ability to bind with high selectivity and/or affinity to virtually any target molecule. In certain embodiments, the targeting moiety binds to a pathogen-associated target molecule, including, but not limited to, surface proteins or antigens from a virus (e.g., HAV, HBV, or HCV, HIV, influenza virus), bacteria, yeast, parasites, or fungus. In other embodiments, the target molecule is a cell surface protein, including but not limited to, a cell surface antigen or receptor from an infected host cell or a tumor cell. Exemplary tumor-associated antigens include the growth factor receptor of the tyrosine kinase family, p185HER2, In other embodiments, the target molecule is a hormone or growth factor. Exemplary hormones or growth factors include tumor necrosis factor alpha (TNFα) or Vascular endothelial growth factor (VEGF). In other embodiments, the target molecule is an antibody (e.g., an auto-antibody).

In one preferred embodiment, the targeting moiety of the invention comprises a peptide moiety. The length of the peptide targeting moiety is desirably between at least 3-200 amino acids, preferably between at least 3-100 amino acids, more preferably between 3-50 amino acids, and still more preferably between 3-30 amino acids (e.g., 3, 4, 5, 6, 7, 8, 9, 10, 11, 12, 13, 14, 15, 16, 17, 18, 19, 20, 21, 22, 23, 24, 25, 26, 27, 28, 29, or 30 amino acids). Exemplary peptides for use as targeting moieties are described in WO/2010/014830, which is herein incorporated by reference in its entirety. In a preferred embodiment, the peptide is a VEGF-binding peptide comprising or consisting of any one or more of the following amino acid sequences, or VEGF-binding portions thereof:

SEQ ID NO. 1
H-Gly-Val-Gln-Glu-Asp-Val-Ser-Ser-Thr-Leu-Gly-Ser-Trp-Val-Leu-Leu-Pro-Phe-His-Arg-Gly-Thr-Arg-Leu-Ser-Val-Trp-Val-Thr

SEQ ID NO. 2
H-Gly-Gly-Phe-Glu-Gly-Leu-Ser-Gln-Ala-Arg-Lys-Asp-Gln-Leu-Trp-Leu-Phe-Leu-Met-Gln-His-Ile-Arg-Ser-Tyr-Arg-Thr-Ile-Thr

SEQ ID NO. 3
H-Gly-Val-Gly-Gly-Ser-Arg-Leu-Glu-Ala-Tyr-Lys-Lys-Asp-His-Arg-Val-Phe-Gln-Met-Ala-Trp-Leu-Gln-Tyr-Tyr-Trp-Ser-Thr-Thr;
and/or SEQ ID NO. 4
H-Gly-Ser-Gly-Ser-Gly-Asn-Ala-Leu-His-Trp-Val-Cys-Ala-Ser-Asn-Ile-Cys-Trp-Arg-Thr-Pro-Trp-Ala-Gly-Gln-Leu-Trp-Gly-Leu-Val-Arg-Leu-Thr.

In other embodiments, the targeting moiety of the invention comprises an antibody, or binding fragment thereof (e.g., a CDR (e.g., CDRH3), a variable domain (VH or VL), or a Fab fragment). Any antibody, or fragment thereof, from any animal species, is contemplated for use in the methods and compositions described herein. Suitable antibodies and antibody fragments include, without limitation, single chain antibodies (see e.g., Bird et al. (1988) Science 242:423-426; and Huston et al. (1988) Proc. Natl. Acad. Sci. U.S.A 85:5879-5883, each of which is herein incorporated by reference in its entirety), domain antibodies (see, e.g., U.S. Pat. Nos. 6,291, 158; 6,582,915; 6,593,081; 6,172,197; 6,696,245, each of which is herein incorporated by reference in its entirety), Nanobodies (see, e.g., U.S. Pat. No. 6,765,087, which is herein incorporated by reference in its entirety), and UniBodies (see, e.g., W02007/059782, which is herein incorporated by reference in its entirety In certain embodiments, the antibody is Abciximab, Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Omalizumab, Palivizumab, Panitumumab, Ranibizumab, Rituximab, Tositumomab, Trastuzumab, and/or Golimumab, or antigen binding fragments thereof.

In other embodiments, the targeting moiety of the invention comprises an antibody-like molecule. Suitable antibody-like molecules include, without limitation, Adnectins (see, e.g., WO 2009/083804, which is herein incorporated by reference in its entirety), Affibodies (see, e.g., U.S. Pat. No. 5,831,012, which is herein incorporated by reference in its entirety), DARPins (see, e.g., U.S. Patent Application Publication No. 2004/0132028, which is herein incorporated by reference in its entirety), Anticalins (see, e.g., U.S. Pat. No. 7,250,297, which is herein incorporated by reference in its entirety), Avimers (see, e.g., U.S. Patent Application Publication Nos. 200610286603, which is herein incorporated by reference in its entirety), and Versabodies (see, e.g., U.S. Patent Application Publication No. 2007/0191272, which is hereby incorporated by reference in its entirety).

In other embodiments, the targeting moiety of the invention comprises a ligand for a cell surface receptor, wherein the ligand is capable of recruiting the adaptor molecule to cells that express said cell surface receptor.

In other embodiments, the targeting moiety of the invention comprises the extracellular portion of a cell surface receptor, or fragment thereof, wherein the cell surface receptor, or fragment thereof, is capable of recruiting the adaptor molecule to the cognate ligand of said cell surface receptor. Suitable cell surface receptors include, without limitation, TNF family receptors (e.g., a TNFα receptor, e.g., a human TNFα receptor) and growth factor receptors of the tyrosine kinase family, (e.g, p185HER2).

In certain exemplary embodiments, the targeting moiety of the invention comprises an Fc fusion protein or immunoadhesin (e.g., a TNF receptor-Fc fusion such as Etaneracept).

(b) Ligand Moiety

Ligand moieties of the invention comprise antigenic domains which are bound by Immunoadhesions (Fc fusions proteins) present in a subject. In some embodiments, the ligand moiety is bound by a circulating antibody. Circulating antibodies may be present in the subject due to naturally acquired immunity. Alternatively, the circulating antibodies are present as a result of prior vaccination of the subject. For example, the circulating antibodies may be present as a result of childhood vaccination against small pox, measles, mumps, rubella, herpes, hepatitis and polio. Accordingly, a ligand moiety may comprise one or more epitopes that is recognized by these circulating antibodies.

In some embodiments, however, a ligand moiety interacts with an antibody that has been administered to the subject. For example, an antibody that interacts with the ligand moiety of an adaptor molecule of the invention can be co-administered with the adaptor molecule. Further, the antibody that interacts with ligand moiety may not normally exist in a subject but the subject has acquired the antibody by introduction of a biologic material or antigen (e.g., serum, blood, or tissue) so as to generate a high titer of antibodies in the subject. For example, subjects that undergo blood transfusion acquire numerous antibodies, some of which can interact with a ligand moiety of the adaptor peptide.

A ligand moiety can comprise any compound capable of binding to an antibody, including, without limitation, a peptide, carbohydrate, lipid, antibody, or antibody-like molecule. In some embodiments, a ligand moiety (e.g., a peptide, antibody or antibody-like molecule) can comprise one or more non-natural amino acids. Preferably, the ligand moiety comprises an epitope that binds to a "high-titer antibody." The term "high-titer antibody" as used herein, refers to an antibody that has high affinity for an antigen (e.g., an epitope on an antigenic domain). For example, in a solid-phase enzyme linked immunosorbent assay (ELISA), a high titer antibody corresponds to an antibody present in a serum sample that remains positive in the assay after a dilution of the serum to approximately the range of 1:100-1:1000 in an appropriate dilution buffer. Other dilution ranges include 1:200-1:1000, 1:200-1:900, 1:300-1:900, 1:300-1:800, 1:400-1:800, 1:400-1:700, 1:400-1:600, and the like. In certain embodiments, the ratio between the serum and dilution buffer is approximately: 1:100, 1:150, 1:200, 1:250, 1:300, 1:350, 1:400, 1:450, 1:500, 1:550, 1:600, 1:650, 1:700, 1:750, 1:800, 1:850, 1:900, 1:950, 1:1000.

In certain embodiments, the ligand moieties are antigenic peptides obtained from a known target molecule (e.g., a surface protein from a pathogen, tumor cell, or infected host cell) of the antibody. The length of the peptide ligand moiety is desirably between at least 3-200 amino acids, preferably between at least 3-100 amino acids, more preferably between 3-50 amino acids, and still more preferably between 10-25 amino acids (e.g., 3, 4, 5, 6, 7, 8, 9, 10, 11, 12, 13, 14, 15, 16, 17, 18, 19, 20, 21, 22, 23, 24, 25, 26, 27, 28, 29, or 30 amino acids). In some embodiments, the peptides are comprised of natural amino acids. In other embodiments, the peptides include one or more non-natural amino acids (e.g., D-amino acids).

In certain embodiments, the ligand moiety is a glycosylated ligand moiety. Glycosylated ligand moietics can comprise or consist of an antigenic saccharide or glycan moiety recognized by an antibody in a subject. In some embodiments, the glycosylated ligand moiety is linked directly or indirectly (i.e., via a linker moiety) to the targeting moiety of the adaptor molecule. Such ligand moieties lack an antigenic peptide moiety. In other embodiments, the glycosylated ligand moiety is a glycopeptide comprising additional antigenic peptide elements (e.g., an antigenic domain comprising a peptide or epitope of a pathogen).

Exemplary glycosylated ligand moieties are derived from blood group antigens. These antigens are generally surface markers located on the outside of red blood cell membranes. Most of these surface markers are proteins, however, some are carbohydrates attached to lipids or proteins. Structurally, the blood group determinants that can be used with the embodiments described herein fall into two basic categories known as type I and type II. Type I comprises a backbone comprised of a galactose 1-3 β linked to N-acetyl glucosamine while type II comprises, instead, a 1-4 β linkage between the same building blocks. The position and extent of fucosylation of these backbone structures gives rise to the Lewis-type and H-type specificities. For example, the presence of an a -monofucosyl branch, solely at the C2-hydroxyl in the galactose moiety in the backbone, constitutes the H-type specifity (Types I and II), while further permutation by substitution of a-linked galactose or a-linked N-acetylgalactosamine provides the molecular basis of the familiar serological blood group classifications A, B, and O. By first determining a patient's particular set of blood group antigens, one can select a ligand moiety comprising one or more blood group antigens that are outside of the repertoire of the patient so as to generate a potent response to an adaptor molecule comprising this ligand moiety and thereby redirecting the antibodies present in the patient to target molecule bound by the targeting moiety of said adaptor molecule. Exemplary blood group antigens are set forth in detail in Table 2 of U.S. Pat. No. 7,318,926, which is hereby incorporated by reference in its entirety.

In certain preferred embodiments, the glycosylated ligand moiety comprises one or more gal-α-1-3 gal disaccharide sugar units of the gal antigen. The gal antigen is produced in large amounts on the cells of pigs, mice and New World monkeys by the glycosylation enzyme galactosyltransferase (α(1,3)GT). Since humans and Old World primates lack the gal antigen, they are not immunotolerant to it and produce anti-gal antigen antibodies (anti-Gal) throughout life in response to antigenic stimulation by gastrointestinal bacteria. It has been estimated that anti-gal antibodies represent more than 2% of circulating IgG and 1-8% of circulating IgM in humans. The binding of anti-Gal to gal antigens expressed on glycolipids and glycoproteins on the surface of endothelial cells in donor organs leads to activation of the complement cascade and hyperacute rejection, and also plays an important role in occurrence of complement-independent delayed xenograft rejection. Accordingly, the gal antigen has the ability to generate a potent immune response.

In certain preferred embodiments, the glycosylated ligand moiety to be joined or incorporated into the adaptor molecule consists essentially of one or more Gal-α(1-3)-Gal disaccharide sugar units and lacks any of the remaining portions of the Gal antigen (e.g., GlcNac or Glc). For example, one or more Gal-α(1-3)-Gal disaccharides may be linked to a targeting moiety of an adaptor molecule via a free hydroxyl group at the reducing end of a disaccharide unit (e.g., the hydroxyl group at the C1 carbon of that is not involved in a glycosidic bond). In certain embodiments the Gal disaccharide is linked to the targeting moiety via a spacer moiety (e.g., C1-C6 alkyl spacer) at the free hydroxyl group. Without being limited to any particular theory, it is thought that the Gal-α(1-3)-Gal disaccharide portion of the Gal antigen binds preferentially to anti-Gal antibodies but exhibits limited binding to lectins (e.g., Galectin-3) or other molecules that bind to other portions of the Gal antigen (e.g., the Gal-β(1-4)-GlcNAc moiety). In other embodiments, the glycosylated ligand moiety to be joined or incorporated into adaptor molecule comprises additional sugar residues of the Gal antigen. For example, one or more trisaccharide (Gal-α(1-3)-Gal-β(1-4)-GlcNAc or Gal-α(1-3)-Gal-β(1-4)-Glc), tetrasccharide (Gal-α(1-3)-Gal-β(1-4)-GlcNAc-β(1-3)-Gal) or pentasaccharide (Gal-α(1-3)-Gal-β(1-4)-GlcNAc-β(1-3)-Gal-β(1-4)-Glc) units of the gal antigen may incorporated.

In certain embodiments the gal antigen to be joined or incorporated into an adaptor molecule is selected from gal-α-(1,3) gal series of neoglycoproteins and can include: Gal α 1-3Gal-BSA (3-atom spacer), Gal α 1-3Gal-BSA (14-atom spacer), Gal α 1-3Gal-HSA (3-atom spacer), Gal α 1-3Gal-HSA (14-atom spacer), Gal α 1-3Galβ1-4GlcNAc-BSA (3-atom spacer), Galα1-3Galβ1-4GlcNAc-BSA (14-atom spacer), Gal α 1-3Galβ1-4GlcNAc-HSA (3-atom spacer), Gal α 1-3Galβ1-4GlcNAc-HSA (14-atom spacer), Gal α1-3Gal-Pentasaccharide-BSA (3-atom spacer), and the like. In other embodiments the gal antigen can be selected from gal α (1,3) gal analogue neoglycoproteins, including Gal α 1-3Galβ1-4Glc-BSA (3-atom spacer), Gal α 1-3Galβ1-4Glc-HSA (3-atom spacer), Gala1-3Galβ1-3GlcNAc-BSA (3-atom spacer), Gal α 1-3Galβ1-3GlcNAc-HSA (3-atom spacer), Gal α 1-3Galβ1-4(3-deoxyGlcNAc)-HSA (3-atom spacer), Gal α 1-3Galβ1-4(6-deoxyGlcNAc)-HSA, and the like.

In yet other embodiments, a peptidomimetic of a Gal antigen can be incorporated into an adaptor molecule of the invention. Exemplary peptidomimetics include the αGal-linked glycopeptides Gal-α-YWRY (SEQ ID NO: 5), Gal-α-TWRY (SEQ ID NO: 6) and Gal-α-RWRY (SEQ ID NO: 7). Other peptidomimetics can be identified by screening a randomized library of αGal glycopeptides for anti-Gal antibody binding activity using the methods of Xian et al. (see J. Comb. Chem., 6:126-134 (2004), which is incorporated by reference herein).

Figure 5:
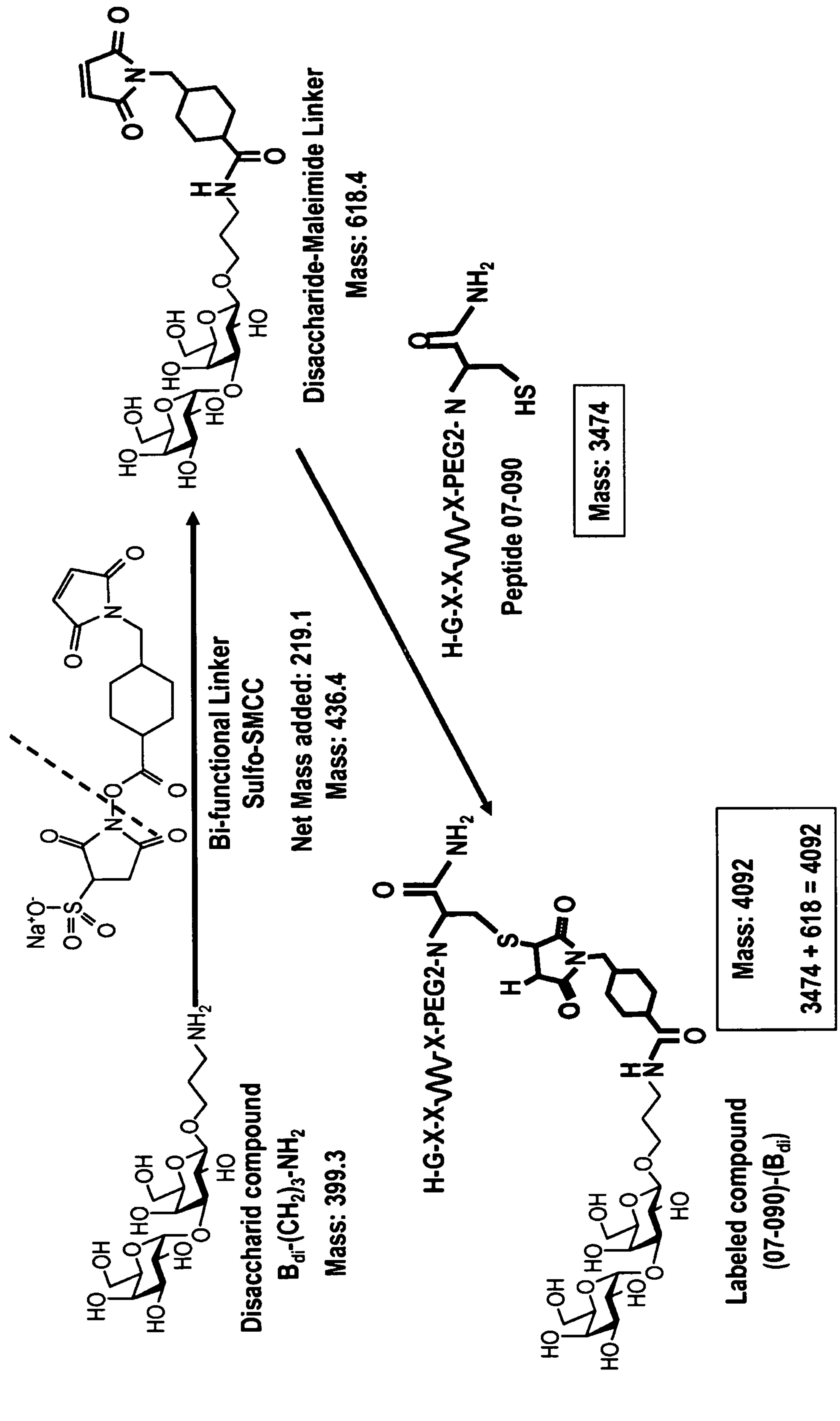
FIG. 5 depicts exemplary methods and linkers for coupling a target moiety (e.g., a VEGF targeting moiety of the invention) to a ligand moiety.
Figure 6:
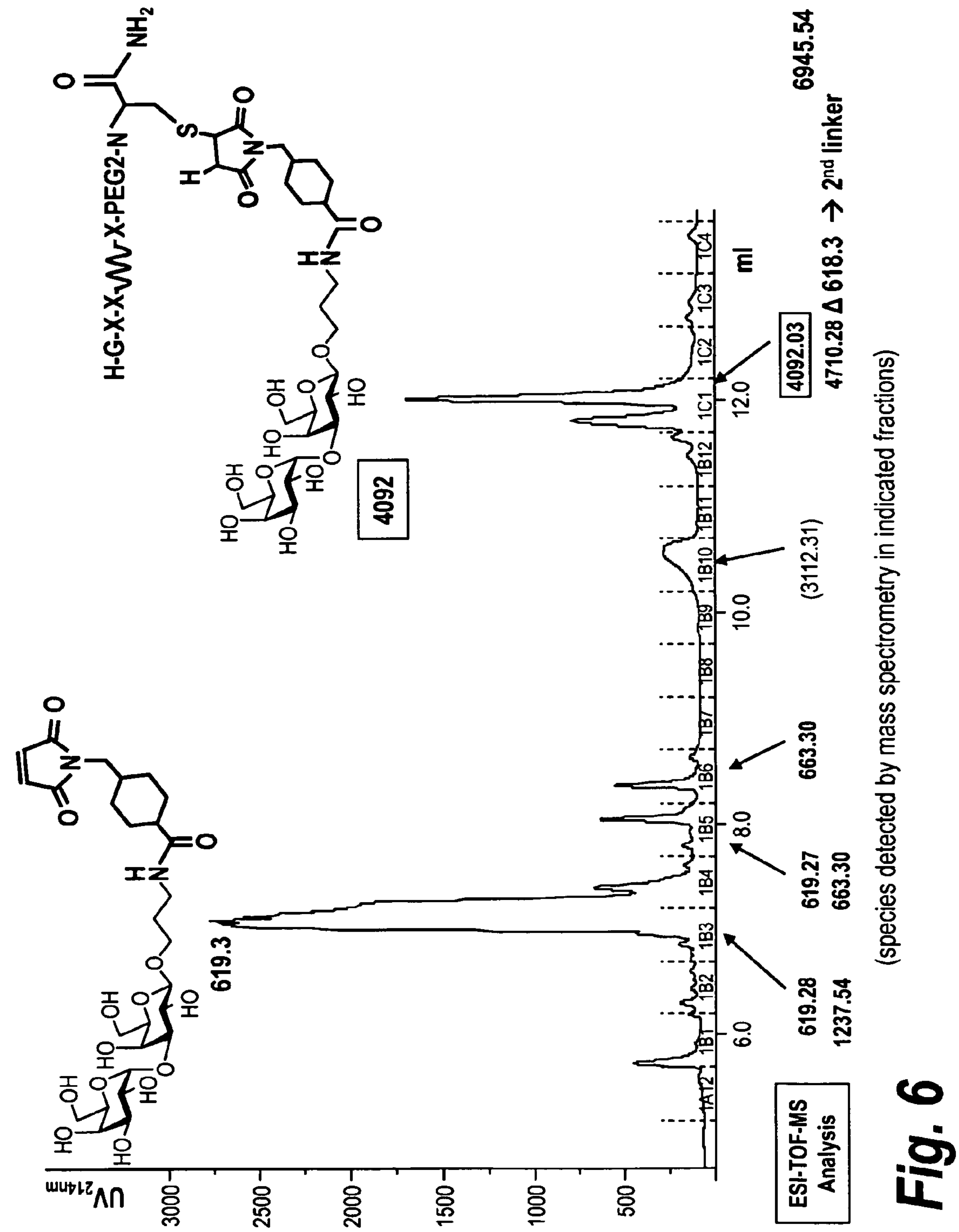
FIG. 6 depicts HPLC and Mass spectrometry analyses of a target moiety/ligand moiety coupling reaction.
Figure 7:
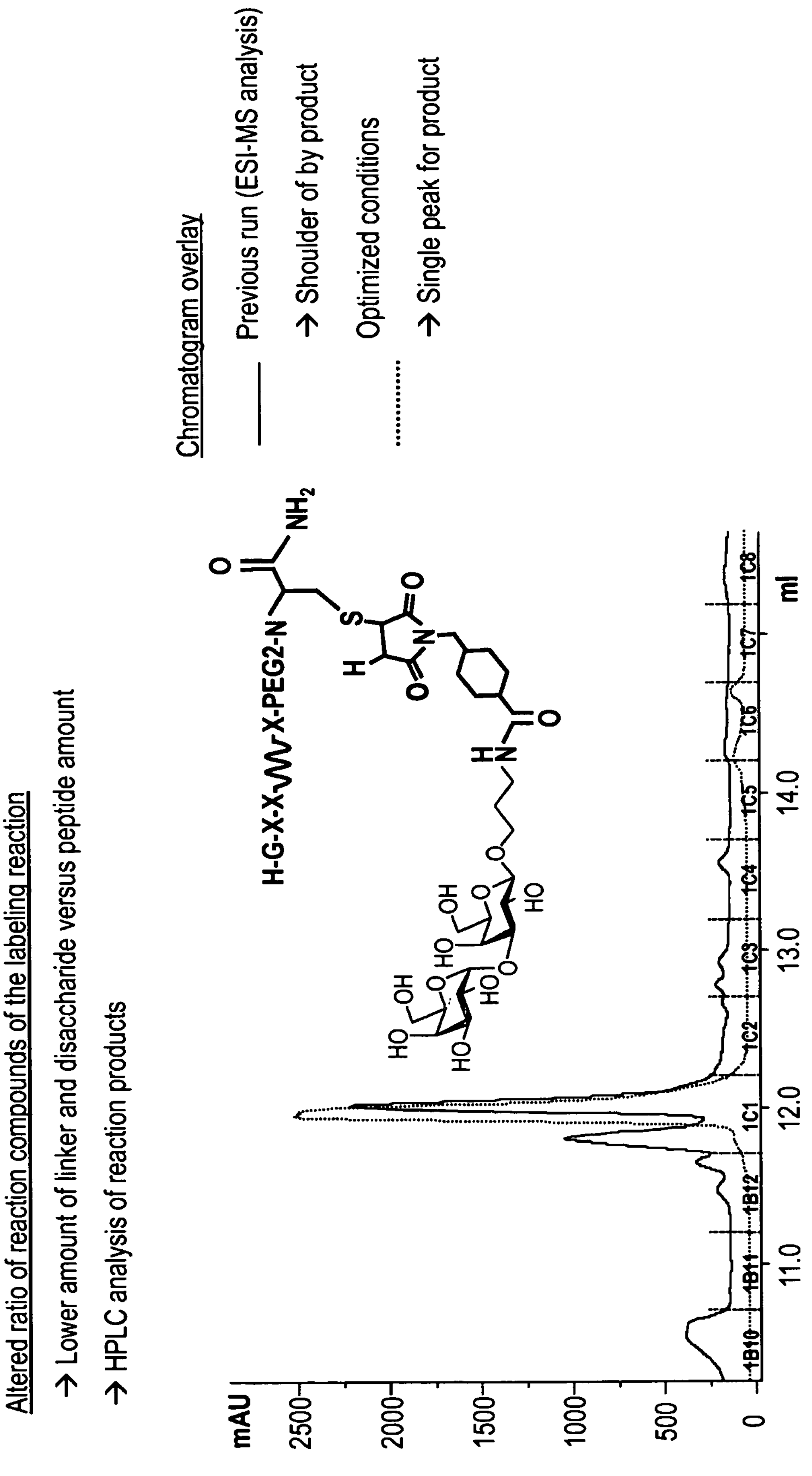
FIG. 7 depicts HPLC and Mass spectrometry analyses of an optimized target moiety/ligand moiety coupling reaction.

A Gal antigen, or peptidomimetic thereof, can be linked to a targeting moiety (covalently and/or non-covalently) using any art-recognized means. Art-recognized non-covalent linkages include biotin-avidin or biotin-streptavidin linkages and other high affinity binding partners (e.g., leucine zippers and the like). Suitable means for covalent attachment include, without limitation, those set forth in FIG. 4 and US Patent Application number 20100183635, which is hereby incorporated by reference in its entirety. For example the gal antigen (or peptidomimeitc) may be linked directly to the polypeptide backbone of a polypeptide targeting moiety via a synthetic chemical linker. Exemplary synthetic chemical linkers include bifunctional linker moieties, e.g., linkers with maleimide functionality. For example, the bifunctional linker moiety may link the targeting moiety and the ligand moiety via an amino group in the targeting moiety and a thiol moiety in the ligand moiety, or vice versa. In one exemplary emobodiment, a maleimide linker (e.g., Sulfo-SMCC) is used to link a cysteine residue of a polypeptide targeting moiety to the amino group of an amino modified Gal antigen (e.g., $B_{di}$—$(CH_2)_3$—$NH_2$ of FIG. 5). Additionally or alternatively, the gal antigen may be linked to N-linked oligosaccharide of a glycoprotein targeting moiety. In some embodiments, one or more Gal antigens (e.g., gal-α-(1,3) gal), or peptidomimetics thereof, are linked to a single site on a target moiety. In other embodiments, one or more Gal antigens.(e.g., gal-α-(1,3) gal), or peptidomimetic thereof, are linked to multiple sites on a target moiety. In certain embodiments, the linker moiety is chemically-modified to reduce enzymatic or chemical degradation.

Adaptor molecules comprising Gal antigen as disclosed herein are particularly advantageous in that they do not appreciably activate basophils, and therefore do not cause an IgE-mediated hypersensitivity reaction when administered to a subject. Notwithstanding, in some embodiments the adaptor molecules of the invention will be assayed for their ability to activate basophils. Suitable assays for measuring basophil activation are known in the art, (see, e.g., J. Allergy Clin Immunol (2002) 110102-9, which is hereby incorporated by reference in its entirety).

In certain embodiments, the ligands moiety comprises polymeric binding molecules wherein the monomers are not amino acids.

In certain exemplary embodiments, the high affinity adaptor molecule is selected from the group consisting of:

(a) (SEQ ID NO:1)-X-Y, comprising: H-Gly-D-Val-D-Gln-D-Glu-D-Asp-D-Val-D-Ser-D-Ser-D-Thr-D-Leu-Gly-D-Ser-D-Trp-D-Val-D-Leu-D-Leu-D-Pro-D-Phe-D-His-D-Arg-Gly-D-Thr-D-Arg-D-Leu-D-Ser-D-Val-D-Trp-D-Val-D-Thr-$PEG_2$-Cys-X-Y;

(b) (SEQ ID NO:2)-X-Y, comprising: H-Gly-Gly-D-Phe-D-Glu-Gly-D-Leu-D-Ser-D-Gln-D-Ala-D-Arg-D-Lys-D-Asp-D-Gln-D-Leu-D-Trp-D-Leu-D-Phe-D-Leu-D-Met-D-Gln-D-His-D-Ile-D-Arg-D-Ser-D-Ser-D-Tyr-D-Arg-D-Thr-D-Ile-D-Thr-$PEG_2$-Cys-X-Y;

(c) (SEQ ID NO:3)-X-Y, comprising: H-Gly-D-Val-Gly-Gly-D-Ser-D-Arg-D-Leu-D-Glu-D-Ala-D-Tyr-D-Lys-D-Lys-D-Asp-D-His-D-Arg-D-Val-D-Phe-D-Gln-D-Met-D-Ala-D-Trp-D-Leu-D-Gln-D-Tyr-D-Tyr-D-Trp-D-Ser-D-Thr-D-Thr-PEG2-Cys-X-Y; and (d) (SEQ ID NO:4)-X-Y, comprising: H-Gly-D-Ser-Gly-D-Ser-Gly-D-Asn-D-Ala-D-Leu-D-His-D-Trp-D-Val-D-Cys-D-Ala-D-Ser-D-Asn-D-Ile-D-Cys-D-Trp-D-Arg-D-Thr-D-Pro-D-Trp-D-Ala-Gly-D-Gln-D-Leu-D-Trp-Gly-D-Leu-D-Val-D-Arg-D-Leu-D-Thr-PEG2-Cys-X-Y;

wherein, X is bifunctional chemical linker with maleimide functionality; and Y is an amino modified Gal-1-3-Gal disaccharide.

(c) Modified Adaptor Molecules

One or more moieties of the adaptor molecules of the invention may be modified. In certain embodiments, a peptide moiety of the adaptor molecule is modified. For example, peptide moieties of an adaptor molecule can be modified to include non-natural amino acids such as those described in U. S. Pat. No. 6,559,126, incorporated herein by reference. For example, the peptides of the invention may be composed of one or more, or most preferably all, amino acids which are D-type optical isomers. These D-peptides have several advantages with respect to antibodies and other protein therapeutics. The smaller size and greater stability of the D-peptides makes them simpler to formulate for pulmonary, topical and oral delivery. D-peptides are also known to be poor immunogens (Dintzis et al. (1993) PROTEINS: Structure, Function, and Genetics 16, 306-308). Furthermore, their resistance to enzymatic degradation, and their ability to be combined with polymers, results in enhanced pharmacokinetics compared to other peptide drugs. Also, D-peptides have reduced manufacturing costs that could be passed on to the consumer.

The peptide component of an adaptor molecule can also be modified by any variety of standard chemical methods (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Adaptor molecules of the invention may be designed to include chemical modifications or particular amino acid sequences which promote solubility. For example, in some embodiments peptide moieties may be synthesized to include the amino acids DDD or KKK in the N-terminal or C-terminal regions. Additionally or alternatively, peptides and other targeting moieties may be synthesized to include a PEGylation moiety at, for example, the N-terminal and/or -C terminal regions. Exemplary PEGylation moieties include $PEG_2$-NH2 and $PEG_2$-Cys-NH2 moieties.

The present invention also encompasses "conservative sequence modifications" or "conservative amino acid modifications" of the sequences described herein, i.e., amino acid sequence modifications which do not significantly affect or alter the binding characteristics of the peptide encoded by the nucleotide sequence or containing the amino acid sequence. Such conservative sequence modifications include nucleotide and amino acid substitutions, additions and deletions. Modifications can be introduced into sequences by standard techniques known in the art, such as site-directed mutagenesis and PCR-mediated mutagenesis. In some embodiments, the modifications are chosen by rational design, and the designed peptides are generated by chemical synthesis as described herein. "Conservative amino acid modifications" includes conservative amino acid substitutions which are substitutions in which the amino acid residue is replaced with an amino acid residue having a similar side chain (e.g., similar size, shape, electric charge, chemical properties including the ability to form covalent or hydrogen bonds, or the like). Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

A peptide or mimetic thereof of the invention may be modified by one or more substitutions, particularly in portions of the protein that are not expected to interact with a target protein. It is expected that as many as 5%, 10%, 20%, 30%, 40%, 50%, or even 50% or more of the amino acids in peptide may be altered by a conservative substitution without substantially altering the affinity of the protein for target. It may be that such changes will alter the immunogenicity of the polypeptide in vivo, and where the immunogenicity is decreased, such changes will be desirable. Further non-limiting examples of homologous substitutions that can be made in the structures of the peptidic molecules of the invention include substitution of D-phenylalanine with D-tyrosine, D-pyridylalanine or D-homophenylalanine,.substitution of D-leucine with D-valine or other natural or non-natural amino acid having an aliphatic side chain and/or substitution of D-valine with D-leucine or other natural or non-natural amino acid having an aliphatic side chain. In some embodiments, conservative amino acid substitutions alone, i.e., without amino acid deletions or additions are the preferred type of amino acid modification. One of skill in the art will appreciate that such modifications or substitutions may be made at the DNA level, thus encoding the altered or substituted peptide, or they may be made at the protein level, e.g., by direct chemical synthesis.

In some embodiments a peptide or peptide moiety of an adaptor molecule may be made cyclic. Such "cyclic peptides" have intramolecular links which connect two amino acids. Cyclic peptides are often resistant to proteolytic degradation and are thus good candidates for oral administration. The intramolecular linkage may encompass intermediate linkage groups or may involve direct covalent bonding between amino acid residues. In some embodiments, the N-terminal and C-terminal amino acids are linked. In other embodiments, one or more internal amino acids participate in the cyclization. Other methods known in the art may be employed to cyclize peptides of the invention. For example, cyclic peptides may be formed via side-chain Azide-Alkyne 1,3-dipolar cycloaddition (Cantel et al. *J. Org. Chem.,* 73 (15), 5663-5674, 2008, incorporated herein by reference). Cyclization of peptides may also be achieved, e.g., by the methods disclosed in U.S. Pat. Nos. 5,596,078; 4,033,940; 4,216,141; 4,271,068; 5,726,287; 5,922,680; 5,990,273; 6,242,565; and Scott et al. PNAS. 1999, vol. 96 no. 24 P. 13638-13643, which are all incorporated herein by reference. In some embodiments the intramolecular link is a disulfide bond mimic or disulfide bond mimetic which preserves the structure that would be otherwise be created by a disulfide bond.

In some particularly preferred embodiments, the cyclization of peptides occurs via intramolecular disulfide bonds. In some preferred embodiments, the formation of an intramolecular disulfide bond increases the affinity of the peptide. Accordingly, the methodology used to select and/or affinity mature the peptides or mimetics thereof of the invention may be performed under conditions which allow disulfide bond formation prior to and during selection (e.g., oxidizing conditions). In some particularly preferred embodiments the disulfide bonds may form between cysteine residues which naturally exist in the library or peptide, or which are introduced by the mutation process during one or more rounds of selection. In other embodiments the peptides may be designed to contain cysteine residues at particular positions such that it is known which residues participate in the disulfide bond. Intramolecular disulfide bonding between cysteine residues may be induced by methods known in the art (e.g., U.S. Pat. Nos. 4,572,798; 6,083,715; 6,027,888, and WIPO Publication WO/2002/103024 which are incorporated herein by reference).

In some embodiments, the formation of a disulfide bond (or the formation of a cyclized or intramolecularly linked structure in general) imparts a particular structure onto the peptide which is important for target binding. Accordingly, the disulfide bonds and/or cyclization preferably form prior to peptide selection such that the potentially favorable structure created by bond formation may be selected for. In some embodiments the peptides or mimetics thereof of the invention may have more than one, two, three, or more disulfide bonds. Further methods known in the art to generate, and select peptides with intramolecular di-sulfide bonds, intramolecular di-sulfide bond substitutes, and other intramolecular links may be employed. For example, the methods described in WO03040168, incorporated herein by reference, describe methods to generate and select peptide apatamers, conotides, and other cyclic peptides which, in some embodiments, may be employed with the methods of the present invention.

In related embodiments a peptide conformation or structure which is beneficial to binding (e.g., it increases binding affinity) may be preserved or mimicked by chemical crosslinking or other methods of peptide stabilization. For example, a beneficial peptide conformation or structure which is formed by disulfide bonds may be stabilized by chemical treatment or reaction, thus allowing the preservation of the structure without a disulfide bond. Indeed, peptide stabilization techniques may be employed to stabilize peptides of the invention whether or not a disulfide bond was originally present. For example, the techniques described in Jackson, et al. *J. Am. Chem. Soc.* 1991, 113, 9391-9392; Phelan, et al. *J. Am. Chem. Soc.* 1997, 119, 455-460; Bracken, et al. *J. Am. Chem. Soc.* 1994, 116, 6431-6432, which are incorporated herein by reference, may be used to stabilize peptides or peptide moieties of the invention.

Other methods to stabilize peptides and peptide structures may be used, e.g., olefinic cross-linking of helices through O-allyl serine residues (Blackwell, H. E.; Grubbs, R. H. *Angew. Chem., Int. Ed.* 1998, 37, 3281-3284, incorporated herein by reference), all-hydrocarbon cross-linking (Schafmeister and Verdine *J. Am. Chem. Soc.* 2000, 122 (24), 5891-5892, incorporated herein by reference) and the methods disclosed in U.S. Pat. No. 7,183,059 (incorporated herein by reference). The methods disclosed in Blackwell et al. and Schafmeister et al. may be described as producing "stapled" peptides, i.e., peptides which are covalently locked into a particular conformational state or secondary structure, or peptides which have a particular intramolecular covalent linkage which predisposes them to form a particular conformation or structure. If a peptide thus treated is predisposed to, e.g., form an alpha-helix which is important for target binding, then the energetic threshold for binding will be lowered. Such "stapled" peptides have been shown to be resistant to proteases and may also be designed to cross the cellular membrane more effectively (also see Walensky et al. Science 2004: Vol. 305. no. 5689, pp. 1466-1470; Bernal et al. J Am Chem Soc. 2007, 129(9):2456-7 which are incorporated herein by reference). Accordingly, peptides or peptide moieties of the invention may be thus stapled or otherwise modified to lock them into a specific conformational shape or they may be modified to be predisposed to particular conformation or secondary structure which is beneficial for binding. It is contemplated that such peptide modifications may occur prior to peptide selection such that the benefit of any conformational constraints may also be selected for. Alternatively, in some embodiments, the modifications may be made after selection to preserve a conformation known to be beneficial to binding or to further enhance a peptide candidate.

In other embodiments, the ligand moiety of an adaptor molecule can be modified. Said modifications can be made, for example, to minimize competitive binding by interfering molecules or reduce enzymatic or chemical degradation of the ligand moiety (e.g., under physiological conditions). As used herein, the term "interfering molecule" refers to a binding molecule (e.g., a circulating or cell surface receptor) that competes with circulating antibodies for binding to an adaptor molecule and prevents it from exerting its intended therapeutic effect (e.g., by rapidly clearing the adaptor molecule from circulation). For example, a glycosylated ligand moiety may comprise a gal antigen or mimetic that has been chemically-modified to enhance preferential binding by anti-Gal antibodies while minimizing undesirable binding by a lectin (e.g., Galectin-3) or other interfering molecule. Additionally or alternatively, a glycosylated ligand moiety may comprise a gal antigen or mimetic that has been chemically-modified, for example, to reduce enzymatic or chemical degradation or facilitate covalent linkage. Exemplary modifications include the addition of biologically inert protecting groups to reactive hydroxyl groups on the sugar residues of a gal antigen, e.g., via dehydrative coupling, reductive amination, or enzymatic oxidation, e.g., with galactose oxidase. Protecting groups may be added to the C-6' OH on the terminal Gal residue of a Gal epitope (see, e.g., Andreana et al., Glycoconjugate J., 20: 107-118 (2004)). Exemplary protecting groups include amine (e.g., aminopyridine) and oxime subsituents (e.g., O-Me-oxime, O-Et-oxime, O-tBu-oxime, O-Bn-oxime and O-allyl-oxime). Alternatively, the polar C-6' OH group can be replaced with a nonpolar hydrogen to form a 6-deoxy-α-Gal derivative (see Janczuk et al., Carbohydrate Research, 337: 1247-1259 (2002), incorporated by reference herein). In certain exemplary embodiments, the Gal epitope can be modified (e.g., at the C-1 OH) with an amino modifier (e.g., alkyl-NH2 substithent) to facilitate linkage to a targeting moiety. Binding of anti-Gal antibodies to the modified gal antigen can then be evaluated using art-recognized methodologies (e.g., ELISA).

(d) Multivalent Adaptor Molecules

It is contemplated that a plurality of peptides or peptide moieties of the sort disclosed herein could be connected to create a composite adaptor molecule with increased avidity or valency. Likewise, a peptide or peptide moiety of an adaptor molecule may be attached to any number of other polypeptides, such as fluorescent polypeptides, targeting polypeptides and polypeptides having a distinct therapeutic effect.

II. Methods for Identifying High Affinity Adaptor Molecules

In certain aspects, the invention provides methods for identifying an adaptor molecule with high binding affinity or selectivity. The methods of the invention comprise (i) at least one selection step to identify a high affinity targeting moiety (e.g., a targeting peptide moiety and/or ligand peptide moiety), and (ii) and a linking step wherein the targeting and ligand moieties of the adaptor molecule are linked to form the adaptor molecule.

Figure 2:
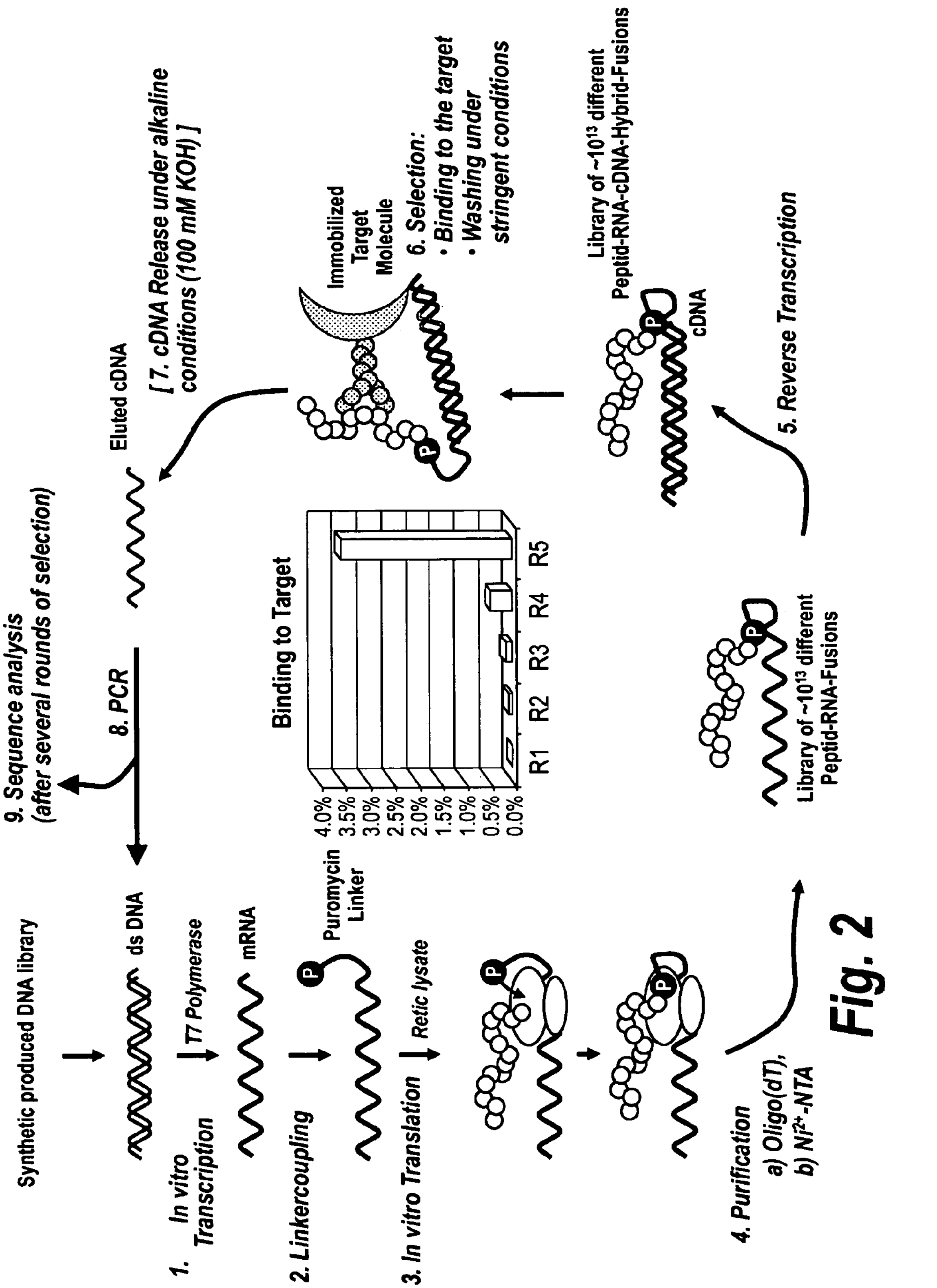
FIG. 2 provides an overview of the various method steps conducted during mRNA display.

In certain embodiments, the methods of the invention employ ribosome or mRNA display as a selection step to identify one or more targeting moieties of an adaptor molecule. A general overview of ribosome and mRNA display methods is provided by Lipovsek and Pluckthun (J. Immunological Methods, 290: 51-67 (2004)), hereby incorporated by reference in its entirety. In preferred embodiments, the targeting moiety (e.g., a peptide targeting moiety) of the adapator molecule is identified using mRNA display. An exemplary mRNA display methodology is depicted in FIG. 2. Briefly, a starting library is obtained by, e.g., direct DNA synthesis or through in-vitro or in-vivo mutagenesis. The double stranded DNA library is then transcribed in-vitro (e.g., using T7 polymerase) and attached to a puromycin-like linker. In vitro translation is carried out wherein the puromycin-like linker reacts with the nascent translation product. The result, after purification, is a highly diverse (~$10^{13}$) library of peptide-RNA fusion molecules. Reverse transcription generates a cDNA/RNA hybrid, covalently linked to the transcribed peptide. This complex is then selected for by using the target molecule (in the case of a targeting peptide moiety) or an antibody (in the case of a ligand peptide moiety). Peptides that bind the target or antibody molecule (e.g., under stringent wash conditions) will be selected, and the cDNA is easily eluted to identify the selected peptides. The selection can be performed multiple times to identify high affinity binders. It should be noted that the selection methodology may be carried out under conditions such that intramolecular disulfide bonds are present in the peptides during selections. In other embodiments, the formation of disulfide bonds may be prevented, if desired.

In additional or alternative embodiments, the methods of the invention employ phage display and/or yeast display techniques as a selection step to identify one or more targeting (e.g., peptide) moieties of an adaptor molecule. Non-limiting examples of such library screening methods are described, for example, in U.S. Pat. Nos. 7,195,880; 6,951,725; 7,078,197; 7,022,479; 5,922,545; 5,830,721; 5,605,793, 5,830,650; 6,194,550; 6,699,658, each of which is herein incorporated by reference in its entirety.

In other embodiments, the methods of the invention employ libraries of synthetic peptides. Such synthetic peptides can be chemically synthesized or enzymatically produced (e.g., by in vitro translation from RNA or by enzymatic digestion of preexisting proteins). In some embodiments, a library of synthetic peptides is arrayed on a solid substrate (e.g., a glass slide).

Figure 3:
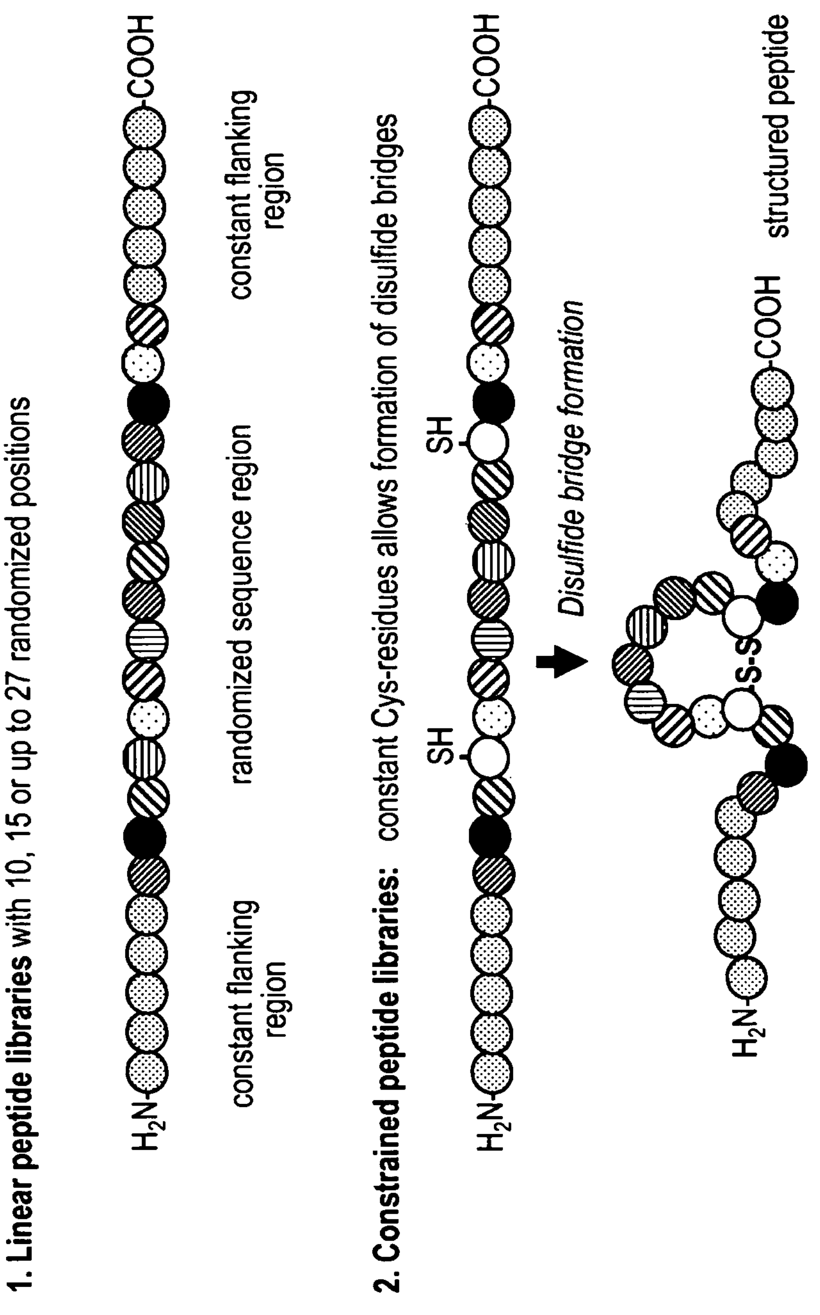
FIG. 3 depicts exemplary peptide libraries that may be used in mRNA display for selection of high affinity adaptor peptides.

In certain embodiments, the methods of the invention employ mRNA libraries (e.g, mRNA display libraries) that encode randomized peptides corresponding to a portion of a larger polypeptide that is known to interact with a particular target or antibody molecule. Exemplary mRNA display libraries are depicted in FIG. 3. For example, a peptide library may comprise a population of linear peptide molecules where the amino acid sequence of the peptides are randomized at one or more amino acid positions (preferably at least 10 or more amino acid positions) within the molecule. This randomized portion of the peptide sequence may be flanked by one or more constant regions from the parent polypeptide.

In certain embodiments, the methods of the invention include providing an mRNA display library that encodes a randomized population of candidate targeting moieties (e.g., or peptides or polypeptides). By way of example the targeting peptides may be randomized peptides derived from a soluble ligand, e.g., VEGF. High affinity targeting peptides are selected by screening peptide-RNA-cDNA fusions from the library. Multiple selection cycles are preferably performed to enrich the population of molecules for those that bind to the target molecule (e.g., VEGF receptor). By decreasing the concentration of target molecule in each selection step, the peptides which bind to the target molecule with highest affinity can be further enriched in the population. Additional selection procedures that can be employed in each selection step include: (1) contra-selection to eliminate non-specific peptides; (2) competitive elution to identify site-specific peptides; (3) and selection under specific solution conditions (e.g., highly stringent wash conditions) to identify stable peptides.

In certain embodiments, the members of a library are modified prior to selection to include a coupling moiety which is capable of reacting with a linker (e.g., a bifunctional linker) to form a linking moiety. In other embodiments, the members of the library are modified with a coupling moiety after the selection step to facilitate linkage to the linking moiety. Examplary coupling moieties include terminal amino acids (e.g., C- or N-terminal cysteines or cysteine analogs) or amino acid side chains (e.g., cysteine or cysteine analog side chains) which are capable of reacting with a bifunctional linker of maleimide functionality.

Once a high-affinity targeting moiety has been identified, the peptide can then be linked via a linking moiety to a pre-selected ligand moiety, thereby creating an adaptor molecule. In certain embodiments, the ligand moiety has been pre-selected using mRNA display methods. Alternatively, the targeting moiety can be inserted as a constant region within a second mRNA display library that encodes a randomized population of candidate ligands. This second mRNA display library can then be subjected to further selection steps wherein the library members are screened against an antibody to identify an adaptor molecule. Thus, the candidate ligands preferably correspond to a portion (e.g., an epitope) of an antibody ligand. In one embodiment, an antibody ligand portion can be an epitope of an antigen to which an antibody binds. In another embodiment, the antibody ligand portion can be an idiotope of a first antibody to which a second, anti-idiotypic, antibody binds. In yet another embodiment, the antibody ligand portion can be an Fc binding portion of an Fc binding protein (e.g., an Fc receptor).

Having selected an adaptor molecule that binds with high affinity and/or selectivity to both a target molecule and an antibody molecule, the adaptor molecules can be evaluated for ability to redirect antibody specificity to the target molecule. For example, wherein the target molecule is cell surface molecule, the ability of the adaptor molecule to induce an effector function (e.g., antibody-dependent cellular cytotoxicity (ADCC) or complement-dependent cytotoxicity (CDC) and cell killing can be evaluated using art-recognized techniques.

In yet other embodiments, the members of a library are linked to a ligand moiety prior to the selection step. For example, each member of the library to be screened can be derivatized with a Gal antigen and then subjected to a screening step to identify a high affinity adaptor molecule. Said Gal antigens may be linked to terminal amino acids or amino acid side chains of each peptide.

In yet other embodiments, an iterative selection process may be employed wherein a targeting moiety is selected in a first selection step (or first series of selection steps) and the sequence of the targeting moiety is incorporated into the constant region of an mRNA-peptide fusion to facilitate the selection of a ligand moiety in a second selection step (or second series of selection steps). For example, the first and second selection steps (or series of selection steps) can be alternated in consecutive rounds of selection to identify high affinity adaptor molecules.

III. Methods for Synthesizing a High Affinity Adaptor Molecule.

Once the components of a high affinity adaptor molecule have been identified using the methods described herein, they may be produced using standard methods known in the art. For example, peptides may be produced by recombinant DNA methods, inserting a nucleic acid sequence (e.g., a cDNA) encoding the polypeptide into a recombinant expression vector and expressing the DNA sequence under conditions promoting expression. General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. Appropriate cloning and expression vectors for use with bacterial, fungal, yeast, and mammalian cellular hosts can be found in Cloning Vectors: A Laboratory Manual, (Elsevier, N.Y., 1985), the relevant disclosure of which is hereby incorporated by reference. Other recombinant DNA methods are described in U.S. Pat. Nos. 4,356,270 4,399,216, 4,506,013, 4,503,142, 4,952,682, 5,618,676, 5,854,018, 5,856,123, 5,919,651, and 6,455,275, which are all incorporated herein by reference.

Adaptor molecules and their components may also be made by chemical synthesis, using techniques that are well-known in the art. For example, D-peptides can be synthesized using stepwise addition of D-amino acids in a solid-phase synthesis method involving the use of appropriate protective groups. Solid phase peptide synthesis techniques commonly used for L-peptides are described by Meinhofer, Hormonal Proteins and Peptides, vol. 2, (New York 1983); Kent, et al., Ann. Rev. Biochem., 57:957 (1988); Bodanszky et al., Peptide Synthesis, (2d ed. 1976); Atherton et al. (1989) Oxford, England: IRL Press. ISBN 0199630674; Stewart et al. (1984). 2nd edition, Rockford: Pierce Chemical Company, 91, ISBN 0935940030; and Merrifield (1963) J. Am. Chem. Soc. 85: 2149-2154 all of these references are incorporated herein by reference. D-amino acids for use in the solid-phase synthesis of D-peptides can be obtained from a number of commercial sources. D-peptides and peptides that contain mixed L- and D-amino acids are known in the art. Also, peptides containing exclusively D-amino acids (D-peptides) have been synthesized. See Zawadzke et al., J. Am. Chem. Soc., 114:4002-4003 (1992); Milton et al., Science 256: 1445-1448 (1992). Additional methods to make D-peptides have been described in the art and can be found at least in WIPO Publication No. WO/1997/013522, and U.S. Application No. 60/005,508, which are both incorporated herein by reference.

The peptide of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, the peptides may be exchanged into different buffers and/or concentrated by any of a variety of methods known to the art, including, but not limited to, filtration and dialysis. The purified polypeptide is preferably at least 85% or 90% pure, more preferably at least 93% or 95% pure, and most preferably at least 97%, 98%, or 99% pure. Regardless of the exact numerical value of the purity, the peptide is sufficiently pure for use as a pharmaceutical product.

Exemplification

The present disclosure is further illustrated by the figures and the following examples, which should not be construed as further limiting. The contents of all figures and all references, patents and published patent applications cited throughout this application are expressly incorporated herein by reference in their entireties.

EXAMPLE 1

Selection of High Affinity Anti-VEGF Peptides as Targeting Moiety and Conjugation to an αGal Ligand Moiety Using the mRNA display method depicted in FIG. 2, a library of randomized peptide sequence were screened for high affinity binding to VEGF. Four high affinity anti-VEGF peptide sequences (SEQ ID NOs 1-4) were selected. Each peptide was PEGylated at the C-terminus with $PEG_2$-NH2 or $PEG_2$-Cys-NH2 moiety (see FIG. 4) to facilitate chemical coupling to Gal antigen (Bdi-(CH2)-NH2, disacchride).

To facilitate chemical conjugation of each peptide to the Gal disaccharide, a bifunctional linker with maleimide and sulfo-NHS functionalities (Sulfo-SMCC, PIERCE) was employed. The linker was reacted with the amino group present in the disaccharide and a maleimide functionality in a sulfhydroxyl group of the C-terminal cysteine residues of the peptide. To obtain the desired compound and avoid any further reaction and formation of by-products, the reaction was subjected to RP-HPLC purification right after incubation. Ratios for amounts of reactants were optimized to avoid formation of by-products. In an exemplary synthesis, 6 mg Disaccharide compund $B_{di}$—$(CH_2)$—$NH_2$ (~15 μmol) was dissolved in 100μl 0.1 M Hepes buffer containg 20% MeCN, pH 6.0; 1.3 mg Sulfo-SMCC Linker (~3 μmol) was dissolved in 100 μl 0.1 M Hepes buffer containing 20% MeCN, pH 6.0; and both solutions were mixed and incubated at room temperature for 30 min under continuous rotation of the reaction tube. 1 mg peptide 07-090 (07-090; lyophilisate, TFA adduct, M.W. 3474 g/mol; ~320 nmol) was dissolved in 1 ml $H_2O$/MeCN 80:20%. Immediately after preparation the clear peptide solution was added to the Linker-Disaccharide solution and incubated at room temperature for additional 90 min under continuous rotation of the reaction tube. The reaction mixture was put on ice and an aliquot was analyzed on a RP-HPLC-C18 column. The desired compound ($B_{di}$—$(CH_2)$—NH-Linker-S-07-090-peptide) was purified by running a HPLC gradient from 0 to 50%; buffer A: $H_2O$/5% MeCN, 0.1% TFA, buffer B: $H_2O$/5% MeCN, 0.1% TFA. HPLC fractions were analyzed after dilution with 65% Methanol, 0.5% formic acid by ESI-TOF-MS analysis and product fractions identified. Relevant product peak fractions were frozen at −80° C. and subsequently lyophilized to complete dryness to harbor the desired compound.

EXAMPLE 2

Figure 8:
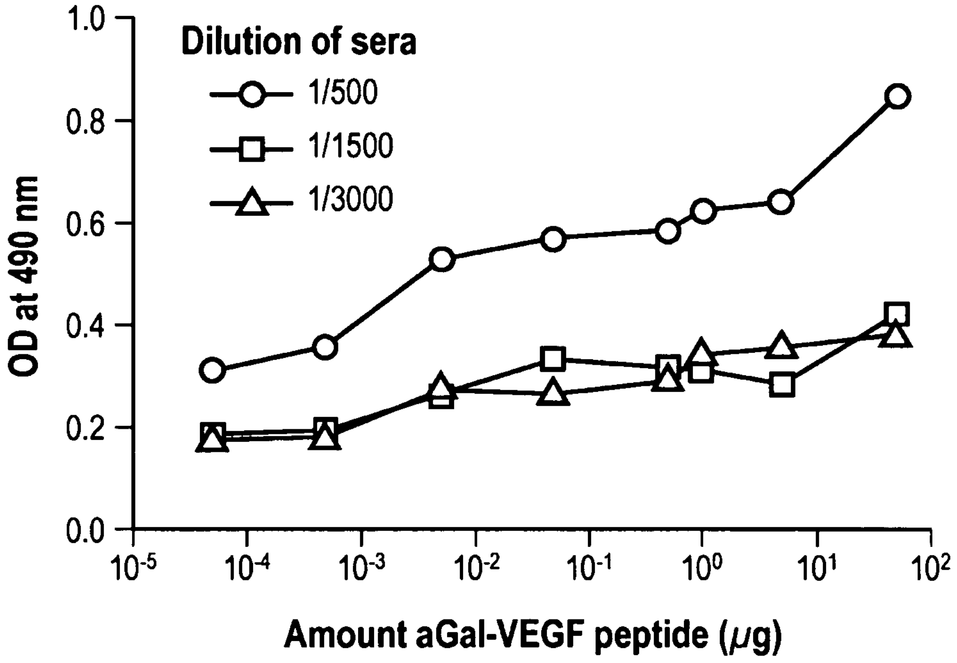
FIG. 8 depicts the results of in vitro assays demonstrating the efficacy of VEGF-binding adaptors of the invention at redirecting naturally occurring anti-gal antibodies to bind VEGF.

Anti-VEGF-specific Adaptor Molecules Can Redirect Natural Anti-αGal Antibodies to VEGF An assay was designed to test the ability of αGal-linked anti-VEGF peptides to redirect natural antibodies, specific for αGal, to bind to VEGF. The assay was designed with recombinant VEGF on the solid phase. A dilution series of αGal-linked anti-VEGF peptides was then incubated with the rVEGF followed by an incubation with sera from mice containing high levels of anti-αGal. The amount of bound anti-αGal was then indicated by an enzyme conjugated anti-mouse antibody. The presence of enzyme was indicated by the addition of a colorometric substrate and the increase in color was measured by determining the optical density at 490 nm. The data, set forth in FIG. 8, clearly shows that the αGal-linked anti-VEGF peptides could redirect natural anti-αGal antibodies to VEGF since a decrease in the amount of peptide or antisera resulted in a decrease in the optical density.

The invention claimed is:

1. A method for identifying a high affinity adaptor molecule capable of redirecting the specificity of a circulating antibody, the method comprising:

(a) providing a randomized library encoding a population of non-naturally occurring candidate targeting peptides, wherein each targeting peptide comprises one or more D-amino acids;

(b) selecting a non-naturally occurring targeting peptide from the library which binds with high affinity and/or selectivity to a cytokine or growth factor target molecule;

(c) linking the non-naturally occurring targeting peptide to a ligand moiety via a linking moiety to form a candidate adaptor molecule, wherein the ligand moiety comprises a glycan moiety or a peptidomimetic thereof; and (d) evaluating the ability of the candidate adaptor molecule to redirect the specificity of the circulating antibody to the cytokine or growth factor target molecule; thereby identifying the adaptor molecule.

2. The method of claim 1, wherein steps (a)-(d) are performed consecutively.

3. The method of claim 1, wherein linking step (c) is performed prior to step (b).

4. The method of claim 1, wherein the library is an mRNA display, ribosome display, yeast display, phage display or synthetic peptide library.

5. The method of claim 1, wherein the targeting peptide binds to the target molecule with a binding affinity of 1 nM or lower.

6. The method of claim 1, wherein the ligand moiety is a blood group antigen.

7. The method of claim 1, wherein the ligand moiety is a gal antigen or epitope thereof.

8. The method of claim 7, wherein the ligand moiety consists of one or more gal-α-1-3-gal disaccharide units.

9. The method of claim 7, wherein the ligand moiety is a modified gal antigen having modifications which reduce competitive binding by interfering molecules.

10. The method of claim 7, wherein the ligand moiety is a modified gal antigen having modifications which reduce enzymatic or chemical degradation.

11. The method of claim 9, wherein the modified gal antigen comprises a protecting group at a C6' position of a terminal galactose residue.

12. The method of claim 1, wherein the ligand moiety is a peptidomimetic of a gal antigen.

13. The method of claim 1, wherein the target molecule is a soluble disease-associated molecule.

14. The method of claim 13, wherein the redirected antibody specificity is evaluated by measuring opsonization or neutralization of the soluble molecule.

15. The method of claim 1, wherein the ligand moiety is linked to the targeting moiety with a bifunctional linker moiety.

16. The method of claim 15, wherein the bifunctional linker moiety links the targeting moiety and the ligand moiety via an amino group in the targeting moiety and a thiol moiety in the ligand moiety.

17. The method of claim 1, wherein the cytokine or growth factor target molecule is present on the surface of an infected or neoplastic cell.

18. The method of claim 17, wherein the redirected antibody specificity is evaluated by measuring ADCC or CDC-dependent killing of the cell.

19. The method of claim 1, wherein the library is an mRNA display library.

20. The method of claim 1, wherein the targeting moiety binds with high affinity or selectivity to VEGF ligand.

* * * * *